United States Patent [19]

Koyama et al.

[11] Patent Number: 4,567,024

[45] Date of Patent: Jan. 28, 1986

[54] ANALYTICAL ELEMENT

[75] Inventors: Mikio Koyama; Kenichiro Okaniwa, both of Hino, Japan

[73] Assignee: Konishiroku Photo Industry Co., Ltd., Tokyo, Japan

[21] Appl. No.: 456,837

[22] Filed: Jan. 10, 1983

[30] Foreign Application Priority Data

Jan. 14, 1982 [JP] Japan .................................... 57-5192

[51] Int. Cl.$^4$ ....................... G01N 21/78; G01N 33/52
[52] U.S. Cl. ........................................ 422/56; 422/57; 435/805
[58] Field of Search ............................. 422/56, 57, 58; 435/805

[56] References Cited

U.S. PATENT DOCUMENTS 4,255,384 3/1981 Kitajima et al. .................. 422/56 X
4,390,343 6/1983 Walter et al. ...................... 422/57 X
4,427,632 1/1984 Okaniwa et al. .................. 422/57 X
4,430,436 2/1984 Koyama et al. ................... 422/57 X

*Primary Examiner*—Arnold Turk
*Attorney, Agent, or Firm*—Frishauf, Holtz, Goodman & Woodward

[57] ABSTRACT

An analytical element comprising a light-transmissive and liquid-impervious support having thereon, in order from the support side, at least one reagent layer containing at least one kind of reagent reactive with a component in a fluid sample, a shielding layer and at least one porous spreading layer, said shielding layer comprising at least a white pigment and a substantially water-dispersible reactive polymer which comprises a copolymer having (i) monomeric units which have a reactive group and (ii) at least one kind of other hydrophobic monomer.

12 Claims, No Drawings

ANALYTICAL ELEMENT

This invention relates generally to analytical chemistry, particularly to an analytical element for analysis of a predetermined specific component in a fluid. More particularly, it pertains to a quantitative analytical element for analysis of a specific component in a biological fluid sample.

There have been developed a large number of methods for analysis of test components in a liquid. These methods may be classified broadly into liquid reaction systems and solid reaction systems.

The analytical reaction in a solution system includes a large number of procedures, varying widely from an analytical procedure of so-called manual method in which no machine is used at all to automatic quantitative analyzer frequently used in recent years in clinical diagnostic chambers.

Among them, automatic quantitative analyzers are useful especially for analysis of blood, and so on.

For example, the analyzer based on the continuous analysis as disclosed in U.S. Pat. No. 2,797,149 is typical of these automatic analyzers.

These analyzers will perform quantitative measurements by mixing a fluid sample, a diluent and an analytical reagent, transferring the mixture into an analytical device, where the analytical reaction and quantitative determination are conducted.

However, these continuous analyzers are complicated and expensive, requiring operational technique by an expert. Repeated cleaning operations are also necessarily required to be performed, for which enormous amounts of time and labor are consumed. In addition, waste liquors from such cleaning operations will inevitably cause the problem of environmental pollution.

On the other hand, there have been widely employed the analytical method in which the dry system reaction (hereinafter abbreviated as dry chemistry) is used.

For example, as disclosed in U.S. Pat. Nos. 3,050,373 or 3,061,523, a water-absorptive carrier such as filter paper is impregnated with a reagent solution and dried to prepare a test strip.

Generally, according to these methods, by adding dropwise a fluid sample on an analytical test paper or merely on a test strip, or by dipping a test strip in a fluid sample, and measuring the color change or density change of the test strip by judgement with naked eyes or by means of a reflection densitometer, the concentration level of a specific component in the fluid sample is determined.

These test strips are useful, since they are easy to handle and can give directly the result of test, but its usefulness is still in the field of semi-quantitative analysis or qualitative analysis due to its constitution.

As contrasted to the analytical method of the prior art as described above, there is also proposed an analytical element of blood as disclosed in Japanese Patent Publication No. 21677/1978, in which dry chemistry easy of handling is utilized, having also a high quantitative performance.

This is an analytical element of blood, comprising at least one reagent layer which is positioned on one side of a light-transmissive and liquid-impervious support, contains at least one reagent reactive with the component in a fluid sample and is constituted of a hydrophilic colloid and at least one spreading layer of a non-fibrous porous spreading layer which is positioned on the reagent layer on the opposite side to that of said support for permitting the component in said fluid sample to permeate into said reagent layer.

The aforesaid analytical element of blood is known to be very useful for biochemical analysis in which a serum is to be employed. However, when whole blood containing blood cell components is applied, it cannot sufficiently shield the red color from the erythrocytes in blood cell components.

For improvement of these points, it is known to provide a color shielding layer between the spreading layer and the reagent layer. These comprise white pigments and hydrophilic colloidal substances, but the color shielding layers having such a constitution have also a great drawback. That is, since film formation is effected with the use of a hydrophilic colloidal substance as binder, a large amount of binder is required to be used. For this reason, the proportion of a white pigment is lowered and the film thickness must be increased in order to obtain a sufficient color shielding effect.

As a consequence, a fluid sample is trapped in the color shielding layer, whereby migration of the sample into the reagent layer is retarded to cause undesirable diffusion, and further there is involved the drawback that a fluid sample cannot sufficiently be supplied to the reagent layer.

As the result of extensive studies made by the present inventors, the above drawbacks have successfully been overcome by use of an analytical element having the following constitution, namely comprising a light-transmissive and liquid-impervious support having thereon at least one reagent layer containing at least one kind of reagent reactive with a component in a fluid sample, a shielding layer and at least one porous spreading layer, in which said shielding layer comprising at least a white pigment and a substantially water-dispersible reactive polymer.

This invention is to be described in further detail below.

The analytical element of this invention not only eliminates the influence of interfering substances in a fluid sample, especially those which interfere with measurement of reflective colorimetric densities (e.g., erythrocytes), but also has the function of permitting a fluid sample to pass quickly through a reagent layer without causing any undesirable stagnation.

The shielding layer of this invention is constituted of at least a white pigment and a substantially water-dispersible polymer, and preferably said polymer contains monomeric units having reactive groups as constituents.

As the white pigment, there may be employed minute particles of chemically inert inorganic or organic pigments or glasses, organic polymers, etc. which are conventionally used. The term "chemically inert" herein used means that these materials do not interfere with the analytical reactions concerned with this invention such as enzymatic reactions, coloration reactions and others. Preferably, there may be employed inorganic pigments as exemplified by titanium dioxide, barium sulfate and the like.

As the substantially water-dispersible polymer (usually called a latex or a polymeric latex; hereinafter referred to merely as the polymer according to this invention), there may be employed any polymer containing monomeric units having reactive groups.

As the monomer having a reactive group, there may be included monomers having epoxy groups, monomers having aziridyl groups, monomers having formyl groups, monomers having hydroxymethyl groups, monomers having isocyanate groups, monomers having thiol groups and precursors thereof, monomers having carbamoyl groups, monomers having hydroxyl groups, monomers having active methylene containing groups, monomers having haloethylsulfonyl groups, monomers having vinylsulfonyl groups and precursors of these monomers.

As a monomer having an epoxy group, there may be mentioned, for example, glycidyl acrylate, glycidyl methacrylate, allyl glycidyl ether, 4-vinylcyclohexane monoepoxide, etc. A monomer having an aziridyl group may be exemplified by aziridylethyl methacrylate, 1-ethylenesulfonyl aziridine, 1-ethylenecarbonyl aziridine, aziridylethyl acrylate, etc. Typical examples of a monomer having a formyl group are acrolein and methacrolein. A monomer having a hydroxymethyl group may include, for example, N-methylol-acrylamide, N-methylol-methacrylamide, N-methyloldiacetoneacrylamide, and the like. Typical examples of a monomer having an isocyanate group are vinyl isocyanate and allyl isocyanate. Examples of a monomer having a thiol group are vinyl thiol, p-thiol styrene, m-thiol styrene, vinyl benzyl thiol and acetyl derivatives of these. As a monomer having a carbamoyl group, there may be included, for example, acrylamide, methacrylamide, maleinamide, diacetone acrylamide, etc.

As a monomer having a hydroxyl group, there may be mentioned 2-hydroxyethyl acrylate, 2-hydroxyethyl methacrylate, 2-hydroxypropyl methacrylate, 2-hydroxypropyl acrylate, etc. A monomer having a haloethylsulfonyl group may be exemplified by chloroethylsulfonylethyl methacrylate, bromoethylsulfonylethyl methacrylate, etc. A typical example of a monomer having a vinylsulfonyl group is vinylsulfonylethyl methacrylate. Examples of a monomer having an active methylene containing group are acryloyl acetone, methacryloyl acetone, 2-acetoacetoxyethyl acrylate and 2-acetoacetoxyethyl methacrylate. As a monomer having a carboxymethoxymethyl group, there may be mentioned, for example, N-carboxymethoxymethyl acrylamide and N-carboxymethoxymethyl methacrylamide.

The monomers having the aforesaid groups may be used either singly to form a homopolymer or as a combination of two or more kinds to form a copolymer. It is also possible to copolymerize these monomers with at least one kind of other hydrophobic monomers.

Examples of other preferable monomers to be copolymerized with the monomers having reactive groups as described above are set forth below.

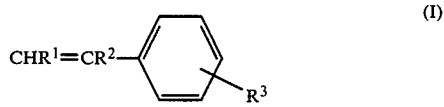
(I)

wherein each of $R^1$ and $R^2$, which can be the same or different, represents a hydrogen atom, a halogen atom, or an alkyl or aryl group having 1 to 10 carbon atoms and $R^3$ represents a hydrogen atom, a halogen atom, or an aliphatic or aromatic group having 1 to 10 carbon atoms. The above-mentioned alkyl group, aryl group, aliphatic group and aromatic group may each be substituted other than amino group. As aliphatic or aromatic groups, there may be included alkyl groups, alkoxy groups, aryl groups and aryloxy groups.

Typical examples of the monomers represented by the formula (I) are styrene, vinyltoluene, vinylbenzyl chloride, t-butylstyrene, etc.

$$CHR^6=CR^4-COOR^5 \quad (II)$$

wherein $R^6$ has the same meaning as $R^1$ in the formula (I), $R^4$ represents a hydrogen atom or a methyl group and $R^5$ represents an aryl or an alkyl group, each having 1 to 10 carbon atoms.

(III) Polymerizable unsaturated nitrile monomers such as acrylonitrile and methacrylonitrile.

(IV) Interparticle crosslinking monomers having two addition-polymerizable groups such as divinylbenzene, N,N-methylene-bis(acrylamide), ethylene diacrylate and ethylene dimethacrylate.

By copolymerization of a suitable combination of these monomers with the aforesaid monomers having reactive groups, it is possible to constitute a compound having a reactive group according to this invention.

The polymer according to this invention may preferably contain 0.5 to 100% by weight of the monomeric units having the above reactive groups and 0 to 99.5% by weight of hydrophobic monomeric units.

As the polymer according to this invention, it is also possible to use a mixture of polymers containing separately monomeric units having two or more kinds of different reactive groups.

Typical examples of the polymer according to this invention are enumerated below, but this invention is not limited thereto.

(1) Glycidyl methacrylate-styrene copolymer (weight ratio 10:90)
(2) Glycidyl methacrylate-n-butyl methacrylate-styrene copolymer (weight ratio 10:15:75)
(3) Glycidyl methacrylate-methyl acrylate-styrene copolymer (weight ratio 5:10:85)
(4) Glycidyl methacrylate-acrylonitrile-ethyl acrylate copolymer (weight ratio 20:5:75)
(5) Glycidyl methacrylate-methyl methacrylate copolymer (weight ratio 30:70)
(6) Glycidyl acrylate-n-butyl acrylate-divinylbenzene copolymer (weight ratio 5:93:2)
(7) Glycidyl acrylate-styrene copolymer (weight ratio 8:92)
(8) Aziridylethyl methacrylate-styrene copolymer (weight ratio 30:70)
(9) Aziridylethyl acrylate-methyl methacrylate copolymer (weight ratio 35:65)
(10) 1-Ethylenesulfonylaziridine-n-butyl methacrylate-styrene copolymer (weight ratio 10:15:75)
(11) 1-Ethylenecarbonylaziridine-acrylonitrile-methyl acrylate copolymer (weight ratio 15:20:65)
(12) Aziridylethyl acrylate-ethyl acrylate copolymer (weight ratio 90:10)
(13) Acrolein-styrene copolymer (weight ratio 5:95)
(14) Acrolein-methyl acrylate-n-butyl acrylate copolymer (weight ratio 5:60:35)
(15) Acrolein-p-methylstyrene-n-butyl acrylate copolymer (weight ratio 3:12:85)
(16) Methacrolein-styrene copolymer (weight ratio 15:85)
(17) Methacrolein-acrylonitrile-methyl acrylate copolymer (weight ratio 3:17:80)
(18) N-methylolacrylamide-methyl methacrylate copolymer (weight ratio 12:88)

(19) N-methylolacrylamide-styrene-divinylbenzene copolymer (weight ratio 5:93:2)
(20) Vinyl isocyanate polymer
(21) Vinyl isocyanate-styrene copolymer (weight ratio 5:95)
(22) Chlorosulfonylethyl acrylate-styrene copolymer (weight ratio 15:85)
(23) Chlorosulfonylethyl methacrylate-ethyl acrylate copolymer (weight ratio 10:90)
(24) Vinylthiol-styrene copolymer (weight ratio 5:95)
(25) Hydroxyethyl methacrylate-methyl methacrylate copolymer (weight ratio 15:85)
(26) Vinylsulfonylethyl acrylate-chloroethylsulfonyl acrylate-styrene copolymer (weight ratio 15:15:70)
(27) 2-Acetoacetoxyethyl methacrylate-ethyl acrylate-styrene copolymer (weight ratio 15:45:40)

The polymers according to this invention can easily be prepared by conventional emulsion polymerization.

In the following, synthesis examples of exemplary polymers of this invention are set forth, but the present invention is not limited thereto.

SYNTHESIS EXAMPLE 1

SYNTHESIS OF EXEMPLARY POLYMER (1)

A four-necked flask of 300 ml capacity equipped with a thermometer, a stirring device, a cooling tube and a nitrogen gas inlet tube was prepared and 150 ml of degassed deionized water, 1.5 ml of Trax H-45 (an anionic surfactant produced by Nippon Oil & Fats Co.; active ingredient 30%), 40.5 g of styrene and 4.5 g of glycidyl methacrylate were added thereinto. While stirring at a stirring speed of 250 rpm under a nitrogen atmosphere, the inner temperature in the flask was elevated to 60° C. Then, while maintaining constantly the stirring speed and the inner temperature, aqueous solutions of 0.15 g of potassium persulfate and 0.08 g of sodium bisulfite, each being dissolved in 10 ml of deionized water, were added at the same time, and the reaction was carried out for 6 hours. After the contents were cooled to room temperature, they were filtered with a No. 3 glass filter to obtain a milky white latex.
Polymerization degree: 99.8%
Viscosity (by B-type viscometer): 2.10 cp

SYNTHESIS EXAMPLE 2

SYNTHESIS OF EXEMPLARY POLYMER (2)

A four-necked flask of 300 ml capacity equipped with a thermometer, a stirring device, a cooling tube and a nitrogen gas inlet tube was prepared and 150 ml of degassed deionized water, 1.5 ml of Trax H-45 (an anionic surfactant produced by Nippon Oil & Fats Co.; active ingredient 30%), 33.75 g of styrene, 6.75 g of n-butyl methacrylate and 4.5 g of glycidyl methacrylate were added thereinto. While stirring at a stirring speed of 250 rpm under a nitrogen atmosphere, the inner temperature in the flask was elevated to 60° C.

Then, while maintaining constantly the stirring speed and the inner temperature, aqueous solutions of 0.15 g of potassium persulfate and 0.08 g of sodium bisulfite, each being dissolved in 10 ml of deionized water, were added at the same time. After the reaction was carried out at an inner temperature of 60° C. with stirring at 250 rpm for 6 hours, the contents were cooled to room temperature and filtered with a No. 3 glass filter to obtain a milky white latex.
Polymerization degree: 99.4%
Viscosity (by B-type viscometer): 2.35 cp

SYNTHESIS EXAMPLE 3

SYNTHESIS OF EXEMPLARY POLYMER (14)

A four-necked flask equipped with a thermometer, a stirring device, a cooling tube and a nitrogen gas inlet tube was charged with 150 ml of degassed deionized water, 1.5 ml of Trax H-45 (an anionic surfactant produced by Nippon Oil & Fats Co.; active ingredient 30%) and 2.25 g of acrolein, and the mixture was stirred at 150 rpm at room temperature under a nitrogen stream for one hour. Then, 27 g of methyl acrylate and 15.75 g of n-butyl acrylate were added to the resultant mixture, followed by elevation of the temperature to 45° C. and the stirring speed to 250 rpm, and aqueous solutions of 0.15 g of potassium persulfate and 0.07 g of sodium bisulfite, each being dissolved in 10 ml of deionized water, were added at the same time to carry out the reaction for 6 hours. Further, the inner temperature was elevated to 60° C., whereat the reaction was continued for additional 2 hours to complete polymerization. Then, the contents were cooled to room temperature and filtered with a No. 3 glass filter to obtain a milky white latex.
Polymerization degree: 99.3%
Viscosity (by B-type viscometer): 2.38 cp The shielding layer according to this invention can be formed by mixing a white pigment with a polymer according to this invention at an appropriate ratio, and laminating the resultant mixture on a reagent layer. The proportions of a white pigment and a polymer according to this invention may be selected variously depending on the purpose, but preferably about 50 to about 99.5% by weight for a white pigment and about 0.5 to about 50% by weight for a polymer according to this invention. More preferably, a white pigment may be about 60 to about 98% by weight and a polymer according to this invention about 2 to about 40% by weight.

Further, it is possible to replace a part of the above polymer according to this invention with hydrophilic colloidal substances. These may amount preferably to about 80% by weight or less of the polymer according to this invention, more preferably about 50% by weight or less.

The layer of this invention may have a thickness which can be varied suitably depending on the content of a white pigment, but it may preferably about 30 to about 2 microns, more preferably about 20 to about 5 microns.

The shielding layer according to this invention may also incorporate other additives such as buffering agents, preservatives, surfactants, etc., depending on the purpose.

Particularly, surfactants may be effectively used as a dispersant for the white pigment and also for controlling the permeation rate when a fluid sample is applied for the element of this invention.

As useful surfactants, there may be employed all surfactants of either ionic (anionic or cationic) or nonionic, but preferably nonionic surfactants are more effective. Examples of nonionic surfactants are polyalkyleneglycol derivatives of alkyl-substituted phenols such as 2,5-di-t-butylphenoxy polyethyleneglycol, p-octylphenoxy polyglycidylether, p-iso-nonylphenoxy polyethylene glycol, and polyalkyleneglycol esters of higher fatty acids. These surfactants have the effect of controlling the permeation speed of a liquid sample into the spreading layer of a fibrous structure simultaneously with the effect of inhibiting generation of undesirable "chromatography phenomenon". Further, as the effect of a surfactant, there is also the effect of alleviating various undesirable influences by proteins contained in a biological fluid sample.

The above surfactant may be employed in an amount which can be widely varied, but generally in an amount of 10 to 0.005% by weight based on the weight of the white pigment and the polymer according to this invention, preferably 6 to 0.05% by weight.

The aforesaid liquid-impervious, light-transmissive support according to the analytical element of this invention (hereinafter abbreviated as the support according to this invention) may be any kind of support, so long as it is impervious to liquids and light-transmissive. For example, various polymeric materials such as cellulose acetate, polyethylene terephthalate, polycarbonate or polystyrene are suitable for the purpose of use. In this case, the above support may have a thickness which can freely be selected, but preferably in the range from about 50 microns to 250 microns. The one side surface on the observation side of the support according to the present invention may also be freely worked depending on the purpose intended. Further, a light-transmissive undercoating layer may also be used in some cases on the side of the support where a reagent layer is to be laminated to improve the adhesion between the reagent layer and the support.

The speading layer of this invention may be selected from any of layers, so long as it is provided with the performances as described in Japanese Patent Publication No. 21677/1978, namely:

(1) To distribute a constant volume of a fluid sample uniformly to a constant volume per unit area through the reagent layer;

(2) To remove substances or factors which interfere with the analytical reactions in the fluid sample;

(3) To effect a background action which reflects the measured light transmitted through the support during spectrophotometric analysis.

Accordingly, the spreading layer according to this invention can perform all the three functions as mentioned above, but the three functions may also suitably be separated by use of the layers having respective functions. Further, it is also possible to use a layer having two of the three functions and a layer having the other remaining function. For example, there may be mentioned a spreading layer of a non-fibrous porous medium called as the brush polymer comprising titanium dioxide and cellulose diacetate as disclosed in the above Patent, and the spreading layers of fibrous structure as disclosed in Japanese Provisional Patent Publication Nos. 24576/1981 and 125847/1982, and Japanese Patent application No. 65446/1981. In particular, the above spreading layer of fibrous structure is particularly useful as a material enabling rapid delivery of blood cells, and further useful for spreading delivery of macromolecules which is one of the objects of this invention.

In the reagent layer to be used in this invention, there may be employed various materials. For example, hydrophilic substances (e.g., gelatin, gelatin derivatives such as acid treated gelatin, polyvinyl alcohol, polyacrylamide, etc.) may generally be used as binders.

Further, a part of the hydrophilic colloidal substance can be replaced with a latex as disclosed in Japanese Provisional Patent Publication Nos. 50393/1979 and 116258/1982, and Japanese patent application No. 177596/1981, etc.

In said reagent layer, there is of course included a reagent for analysis of predetermined specific substance in a fluid sample. For example, to take example of glucose, there are included glucose oxidase and peroxidase as enzymes and a color base such as 4-aminoantipyrine, 1,7-dihydroxynaphthalene, etc. Among these reagents, water-soluble reagents may be added as such, and oil-soluble reagents may be incorporated according to the dispersing method known in the photographic field of the art under the name of the direct dispersing method, the oil protect dispersing method, etc.

Further, said layer may also contain various aids such as surfactants, buffering agents, film hardners, preservatives, etc. depending on the purpose.

The above-mentioned reagent layer, shielding layer and spreading layer according to this invention may be provided by coating consecutively on the support.

The analytical element of this invention can take any desired arrangement among various different arrangements. Further, it is also possible to constitute the analytical element in conformity with the object of this invention by combining the reagent layer of this invention optionally with various functional layers, reagent containing layers and members, as exemplified by the reagent layer, light-reflective layer, subbing layer as disclosed in U.S. Pat. No. 3,992,158, radiation blocking layer as disclosed in U.S. Pat. No. 4,042,335, barrier layer as disclosed in U.S. Pat. No. 4,066,403, registration layer as disclosed in U.S. Pat. No. 4,144,306, migration inhibition layer as disclosed in U.S. Pat. No. 4,166,093, scintillation layer as disclosed in U.S. Pat. No. 4,127,499, scavenging layer as disclosed in Japanese Provisional Patent Publication No. 90859/1980 and rapturable pod-like member as disclosed in U.S. Pat. No. 4,110,079, and the like.

After analysis results are obtained as detectable changes by use of the analytical element of this invention, corresponding to the various detectable changes, measurements are performed according to reflection spectrophotometry, emission spectrophotometry or reflection fluorescence spectrophotometry, or scintillation measurement. The thus obtained measured values can determine the amounts of unknown substances to be tested with reference to the calibration curve previously prepared.

The analytical element of this invention having the constitution as described above can accomplish its object by supplying a fluid sample from the side of the spreading layer and then observing the analytical reaction from the side of the transparent support.

A fluid sample to be applied to the analytical element according to this invention may be used in an amount as desired, but preferably in an amount of about 50 $\mu$l to about 5 $\mu$l, more preferably about 20 $\mu$l to about 5 $\mu$l. Usually, it is preferred to use about 10 $\mu$l of a fluid sample.

The analytical reaction to be employed for the analytical element of this invention may be determined suitably depending on the purpose of analysis. For example, it may be used for fields of clinical chemistry, particularly be used for analysis of biological fluid samples such as blood or components in urine.

These can be constituted easily by suitable selection of analytical reagents so as to be available for analysis of a number of components in the various kinds of fluid samples.

This invention is described in further detail by referring to the following Examples, by which the embodiments of the present invention are not limited at all.

EXAMPLE 1

On a transparent polyethyleneterephthalate support with a thickness of 180 microns which had been subjected to a subbing treatment, the following layers were coated consecutively to form a model element.

(1) Model reagent layer (reagent layer containing no reagent):

A reagent layer with a thickness of 28 microns comrpising 11.0 g/m² of a deionized gelatin and 11.0 g/m² of copoly(methyl acrylate/sodium 3-acryloyloxypropane sulfonate/2-acetoacetoxyethyl acrylate) (weight ratio 88.75/4.75/6.5).

(2) Shielding layer:
As described in Table 1.

(3) Spreading layer of a fibrous structure:
A spreading layer of a fibrous structure with a dried film thickness of about 160μ, comprising:

| | |
|---|---|
| Powdery filter paper (C) (produced by Toyo Roshi Co., 300 mesh or larger) | 91.0 g/m²; |
| Copoly(styrene-glycidyl methacrylate) | 13.0 g/m²; and |
| Emulgen (polyoxyethylene lauryl ether; produced by Kao-Atlas Co.) | 0.3 g/m². |

TABLE 1

| Element No. | White pigment | Binder | Film thickness |
|---|---|---|---|
| Model element of this invention (1) | Titanium dioxide | Exemplary polymer (1) 2.2 g/m² | about 10μ |
| Model element of this invention (2) | Titanium dioxide | Exemplary polymer (1) 0.75 g/m² | about 10μ |
| Model element of this invention (3) | Titanium dioxide | Exemplary polymer (1) 1 g/m² Deionized gelatin 1 g/m² | about 10μ |
| Model element of this invention (4) | Titanium dioxide 22 g/m² | Exemplary polymer (14) 1.5 g/m² | about 10μ |
| Model element of this invention (5) | Titanium dioxide 22 g/m² | Exemplary polymer (19) 1.5 g/m² | about 10μ |
| Control model element (1) | Titanium dioxide | Deionized gelatin 2.2 g/m² | about 10μ |
| Control model element (2) | Titanium dioxide | Deionized gelatin 5.5 g/m² | about 18μ |

Onto the above model elements (1) to (5) of this invention and the Control model elements (1) and (2), 10 microliters of a whole blood with a hematocrit value of 40% were added dropwise from the side of the spreading layer of a fibrous structure, and the reflective densities before and after the dropwise addition were measured by a Sakura Photoelectric Densitometer Model PDA-65 (produced by Konishiroku Photo Industry Co.) using a filter of $\lambda_{max}=490$ nm, to obtain the following results.

TABLE 2

| Element | Before dropwise addition | After dropwise addition |
|---|---|---|
| Model element of this invention (1) | 0.16 | 0.17 |
| Model element of this invention (2) | 0.16 | 0.17 |
| Model element of this invention (3) | 0.16 | 0.16 |
| Model element of this invention (4) | 0.16 | 0.16 |
| Model element of this invention (5) | 0.16 | 0.16 |
| Control model element (1) | 0.16 | 0.54 |
| Control model element (2) | 0.16 | 0.21 |

As apparently seen from Table 2, the control model elements cannot completely shield erythrocytes when a whole blood was added dropwise thereon, unless they have large film thicknesses. In contrast, the model elements of this invention could sufficiently shield erythrocytes, even with thicknesses which were not made so thick.

EXAMPLE 2

On a transparent polyethyleneterephthalate support with a thickness of 180 microns which had been subjected to the subbing treatment, the layers having the following compositions were coated consecutively to prepare an analytical element for analysis of glucose.

(1) Reagent layer:
A reagent layer with a dried film thickness of about 30 microns, comprising:

| | |
|---|---|
| Deionized gelatin | 16 g/m² |
| Copoly(methyl acrylate/sodium 3-acryloyloxypropane sulfonate/ 2-acetoacetoxy ethyl acrylate (weight ratio 88.75/4.75/6.5) | 24.2 g/m² |
| Glucose oxidase | 10000 U/m² |
| Peroxidase | 10000 U/m² |
| 1,7-Dihydroxynaphthalene | 0.66 g/m² |
| 4-Aminoantipyrine hydrochloride | 0.86 g/m² |
| 3,3-Dimethylglutaric acid | 1.96 g/m² |
| Bis(vinylsulfonyl methyl ether) | 0.129 g/m² |

(2) Shielding layer:
A shielding layer with a film thickness of about 12 microns comprising:

| | |
|---|---|
| Titanium dioxide | 30 mg/m² |
| Exemplary copolymer (1) | 1.07 g/m² |
| Emulgen 120 (polyoxyethylene lauryl ether, produced by Kao-Atlas Co.) | 1.55 g/m² |

(3) Spreading layer of a fibrous structure:
A spreading layer of a fibrous structure with a dried film thickness of about 160 microns comprising:

| | |
|---|---|
| Powdery filter paper (CC) (produced by Toyo Roshi Co., 300 mesh or larger) | 91.0 g/m²; |
| Copoly(styrene-glycidyl methacrylate) | 13.0 g/m²; and |
| Emulgen 120 (polyoxyethylene lauryl ether; | 0.3 g/m². |

-continued produced by Kao-Atlas Co.)

Further, as a Control analytical element, there was prepared an element in which the above shielding layer was replaced with a Control shielding layer having the following composition:

(4) Control shielding layer:

A Control shielding layer with a film thickness of about 18 microns comprising:

| Titanium dioxide | 44 g/m² |
|---|---|
| Deionized gelatin | 5.5 g/m² |
| Emulgen 120 | 2.475 g/m² |

Onto the analytical elements of this invention and the Control element thus prepared, 10 μl each of whole bloods with a hematocrit value of about 40% having various glucose concentrations was added, followed by incubation at 37° C. for 7 minutes, and then the reflective densities were measured at 490 nm to obtain the results as shown below.

TABLE 3

| | Reflective density (490 nm) | |
|---|---|---|
| Glucose concentration in whole blood | Analytical element of this invention | Control analytical element |
| 98.3 mg/dl | 0.423 | 0.305 |
| 183.5 mg/dl | 0.663 | 0.455 |
| 250.6 mg/dl | 0.827 | 0.551 |
| 330 mg/dl | 0.981 | 0.643 |
| 405 mg/dl | 1.010 | 0.728 |
| 493.2 mg/dl | 1.238 | 0.745 |

From the above results, it can clearly be seen that the Control analytical element is small in difference between respective concentrations, thus being lower in precision as an analytical element. On the other hand, the analytical element of this invention clearly exhibits good color formation without interference by erythrocytes.

We claim:

1. An analytical element comprising a light-transmissive and liquid-impervious support having thereon, in order from the support side, at least one reagent layer containing at least one kind of reagent reactive with a component in a fluid sample, a shielding layer and at least one porous spreading layer, said shielding layer comprising at least a white pigment and substantially water-dispersible reactive polymer which comprises a copolymer having (i) monomeric units which have a reactive group and (ii) at least one kind of hydrophobic monomer which is not said monomeric units (i).

2. The analytical element according to claim 1 wherein said reactive group of monomeric units is at least one selected from the group consisting of an epoxy group, an aziridyl group, a formyl group, a hydroxymethyl group, an isocyanate group, a thiol group, a carbamoyl group, a hydroxyl group, an active methylene containing group, a haloethylsulfonyl group, a vinylsulfonyl group and precursors of these groups.

3. The analytical element according to claim 1, wherein said copolymer contains said hydrophobic monomer units in an amount up to 99.5% by weight.

4. The analytical element according to claim 1, wherein said copolymer is prepared by emulsion polymerization.

5. The analytical element according to claim 1, wherein said white pigment is selected from the group consisting of minute particles of inorganic pigments, organic pigments, inorganic glasses, organic glasses and organic polymers.

6. The analytical element according to claim 1, wherein said shielding layer consists 50 to 99.5% by weight of a white pigment and 0.5 to 50% by weight of a substantially water-dispersible reactive polymer.

7. The analytical element according to claim 7, wherein said shielding layer consists 60 to 98% by weight of a white pigment and 2 to 40% by weight of a substantially water-dispersible reactive polymer.

8. The analytical element according to claim 1, wherein said shielding layer has a thickness of 30 to 2 microns.

9. The analytical element according to claim 8, wherein said shielding layer has a thickness of 20 to 5 microns.

10. The analytical element according to claim 1, wherein said hydrophobic monomer is selected from the group consisting of:

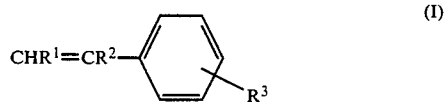

(I)

wherein each of $R^1$ and $R^2$, which can be the same or different, represents a hydrogen atom, a halogen atom, or an alkyl or aryl group having 1 to 10 carbon atoms and $R^3$ represents a hydrogen atom, a halogen atom, or an aliphatic or aromatic group having 1 to 10 carbon atoms, $$CHR^6=CR^4-COOR^5 \quad (II)$$

wherein $R^6$ has the same meaning as $R^1$ in the formula (I), $R^4$ represents a hydrogen atom or a methyl group and $R^5$ represents an aryl or alkyl group, each having 1 to 10 carbon atoms, (III) polymerizable unsaturated nitrile monomers and (IV) interparticle crosslinking monomers having two addition-polymerizable groups.

11. The analytical element according to claim 10, wherein
said reactive group of monomeric units is at least one selected from the group consisting of an epoxy group, an aziridyl group, a formyl group, a hydroxymethyl group, an isocyanate group, a thiol group, a carbamoyl group, a hydroxyl group, an active methylene containing group, a haloethylsulfonyl group, a vinylsulfonyl group and precursors of these groups; and
said copolymer contains said hydrophobic monomer units in an amount up to 99.5% by weight.

12. The analytical element according to claim 11, wherein
said shielding layer consists 60 to 98% by weight of a white pigment and 2 to 40% by weight of a substantially water-dispersible reactive polymer; and
said shielding layer has a thickness of 20 to 5 microns.

* * * * *